United States Patent [19]

Horwitz et al.

[11] 4,266,048
[45] * May 5, 1981

[54] SYNTHESIS OF ANALOGS OF 3'-PHOSPHOADENOSINE 5'-PHOSPHOSULFATE (PAPS)

[75] Inventors: Jerome P. Horwitz; John P. Neenan; Radhey S. Misra; Jurij Rozhin; Anne Huo, all of Detroit, Mich.; Kerstin D. Philips, deceased, late of Detroit, Mich., by J. Christopher Philips, administrator

[73] Assignee: The United States of America as represented by the Department of Health, Education and Welfare, Washington, D.C.

[ * ] Notice: The portion of the term of this patent subsequent to Sep. 25, 1996, has been disclaimed.

[21] Appl. No.: 954,876

[22] Filed: Oct. 26, 1978

Related U.S. Application Data

[63] Continuation-in-part of Ser. No. 840,783, Oct. 11, 1977, Pat. No. 4,169,011.

[51] Int. Cl.³ .................... C07H 19/20; C07H 17/00; C12D 13/06
[52] U.S. Cl. ........................ 536/27; 536/28; 536/29; 435/72
[58] Field of Search ............... 536/26, 27; 195/28 N; 424/180; 435/72

[56] References Cited

U.S. PATENT DOCUMENTS 3,268,416  8/1966  Igarasi et al. .................... 195/28 N
4,169,011  9/1979  Horwitz .......................... 435/72

OTHER PUBLICATIONS

Cherniak et al., J. Biol. Chem., 239(9), 2986–2990 (1964).
Simoncsits et al., Biochem. Biophys. Acta, 395, (1975).
Horwitz, et al., Biochem. Biophys. Acta., 480, 376–381 (1977).

Primary Examiner—Johnnie R. Brown
Assistant Examiner—Blondel Hazel

[57] ABSTRACT

Analogs of 3'-phosphoadenosine 5'-phosphosulfate, also known as PAPS, are useful in establishing sulfate transfer mechanisms in animals and may be produced by a chemical process yielding an analog B of a pure adenosine 2',3'-cyclic phosphate 5'-phosphate, which compound is initially prepared from the reaction of adenosine and pyrophosphoryl chloride. In the present process an analog B is selected from 8-bromoadenine, purine, hypoxanthine, 4-aminopyrrolo[2,3-d]pyrimidine (tubercidin), and 7-amino-pyrazolopyrimidine (formycin). In the pilot procedure the pure cyclic phosphate is reacted with triethylamine-N-sulfonic acid to produce 2',3'-cyclic phosphate 5'-phosphosulfate. Subsequently, by hydrolysis with the enzyme ribonuclease-T₂, the desired compound, an analog of PAPS, is produced. Alternatively, the 2'-phosphoadenosine 5'-phosphosulfate, known as iso-PAPS, may be produced from 2',3'-cyclic phosphate 5'-phosphosulfate by treatment with a different enzyme, PDase II or spleen phosphodiesterase.

5 Claims, No Drawings

SYNTHESIS OF ANALOGS OF 3'-PHOSPHOADENOSINE 5'-PHOSPHOSULFATE (PAPS)

The invention described herein was made in the course of work under a grant or award from the Department of Health, Education, and Welfare.

This is a continuation-in-part application of pending Ser. No. 840,783 filed Oct. 11, 1977, now U.S. Pat. No. 4,169,011, by Jerome P. Horwitz et al entitled "Facile Synthesis of 3'-Phosphoadenosine 5'-Phosphosulfate (PAPS)".

The present invention relates to the synthesis and assay of analogs of 3'-phosphoadenosine 5'-phosphosulfate (PAPS) active as sulfurylation reactions and as substrates for bovine adrenal estrogen sulfotransferase. The adenosine analogs are 8-bromoadenine, purine, hypoxanthine, 4-aminopyrrolo[2,3-d]pyrimidine (tubercidin), and 7-aminopyrazolopyrimidine (formycin).

PRIOR ART STATEMENT

Horwitz et al, "V. Synthesis and Assay of Analogs of 3'-Phosphoadenosine 5'-Phosphosulfate as Substrates for Bovine Adrenal Estrogen Sulfotransferase," [to be submitted for publication].

Cherniak et al, *J. Biological Chemistry*, 239(9): 2986-2990 (1964).

Simoncsits et al, *Biochimica et Biophysica Acta*, 395:74-79 (1975).

Horwitz et al, *Biochimica et Biophysica Acta*, 480:376-381 (1977).

Analogs of adenosine 3'-phosphate 5'-phosphosulfate (PAPS) (IVa) have been prepared by an extension of a method developed by Horwitz et al, *Biochim. Biophys. Acta*, 480:376-381 (1977) using adenosine synthesis of active sulfate; i.e., (IVa). Reaction of the readily accessible ribonucleoside 2',3'-cyclic phosphate 5'-phosphate (II) with triethylamine N-sulfonic acid leads to the requisite mixed anhydride derivative, the ribonucleoside 2',3'-cyclic phosphate 5'-phosphosulfate (III). The latter on treatment with ribonuclease -T2 provides the analog (IV) in high yield as a consequence of regiospecific opening of the cyclic phosphate moiety of (III). Spleen phosphodiesterase, on the other hand, promotes opening of the cyclic phosphate residue of (III) to a (positional isomer) ribonucleoside 2'-phosphate 5'-phosphosulfate (V). In this manner, the 2',3'-cyclic phosphate 5'-phosphates of 8-bromoadenosine (IIb), inosine (IId), nebularine (IIc), tubercidin (IIe) and formycin (IIf) have been converted to corresponding analogs of (IVa) and (Va).

The rate of sulfurylation of estrone relative to (IVa) (RSR=1) as mediated by bovine adrenal estrone sulfotransferase (3'-phosphoadenylyl sulfate: 3-sulfotransferase, EC 2.8.2.4.) is the largest with (IVb) and (IVe) and only minimal with (IVc) and (IVd). The RSR values of (IV), in general, parallel and Ki(s) of corresponding nucleotide coproducts; i.e., the ribonucleoside 3'-5'-diphosphates, suggesting that cosubstrate and coproduct bind to the same enzyme site. The positional isomers (V) do not indicate a corresponding relationship with the related coproduct; i.e., the ribonucleoside 2',5'-diphosphate.

The following schematic illustrates the analogs and the preparation for making them as well as the original preparation using adenine (a).

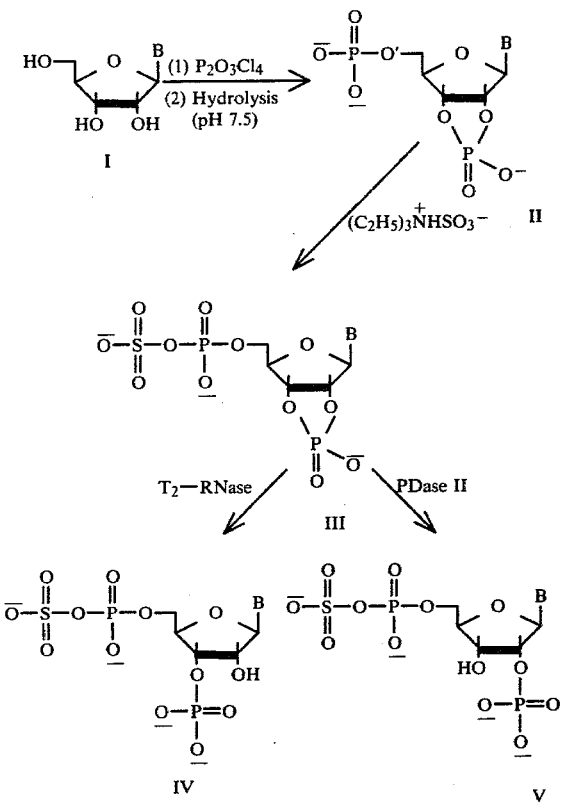

B
(a) adenine
(b) 8-bromoadenine
(c) purine
(d) hypoxanthine
(e) 4-aminopyrrolo[2,3-d]pyrimidine (tubercidin)
(f) 7-aminopyrazolopyrimidine (formycin)

ABBREVIATIONS

3'PAdo5'P=adenosine 3',5'-diphosphate

3'PAdo5'PS=adenosine 3'-phosphate 5'-phosphosulfate (PAPS)

2'PAdo5'P=adenosine 2',5'-diphosphate

2'PAdo5'PS=adenosine 2'-phosphate 5'-phosphosulfate

2':3'PAdo5'P=adenosine 2',3-cyclic phosphate 5'-phosphate

2':3'PAdo5'PS=adenosine 2',3'-cyclic phosphate 5'-phosphosulfate

3'P8-Br-Ado5'P=8-bromoadenosine 3',5'-diphosphate

3'P8Br-Ado5'PS=8-bromoadenosine 3'-phosphate 5'-phosphosulfate

3'PPuo5'P=nebularine (9-β-D-ribofuranosylpurine) 3',5'-diphosphate

3'PPuo5'PS=nebularine 3'-phosphate 5'-phosphosulfate

3'PIno5'P=inosine 3',5'-diphosphate

3'PIno5'PS'=inosine 3'-phosphate 5'-phosphosulfate

3'P(7-deaza-Ado)5'P=tubercidin (4-amino-7-(β-D-ribofuranosyl)-7H-pyrrolo-[2,3-d]-pyrimidine) 3',5'-diphosphate 3'P(7-deaza-Ado)5'PS=tubercidin 3'-phosphate 5'-phosphosulfate 2'P(7-deaza-Ado)5'PS=tubercidin 2'-phosphate 5'-phosphosulfate 3'PFo5'P=formycin (7-amino-3-(β-D ribofuranosyl)-pyrazolo-[4,3-d]-pyrimidine) 3',5'-diphosphate 3'PFo5'PS = formycin 3'-phosphate 5'-phosphosulfate

GENERALIZED PREPARATION

The present invention relates to a practical chemical synthesis of analogs of 3'-phosphoadenosine 5'-phosphosulfate

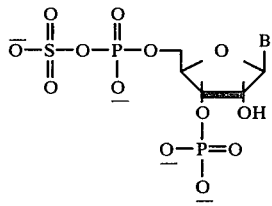 (IV)

in yields of 68–72% from B-2',3'-cyclic phosphate 5'-phosphate

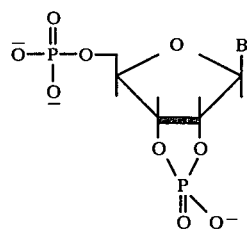 (II)

which is designated the starting material for this process. Compound II may be conveniently prepared by reacting an adenosine analog

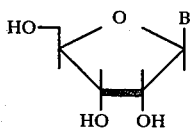 (I)

with pyrophosphoryl chloride under hydrolysis conditions at pH 7.5 to provide a pure starting material. Reaction of II with triethylamine-N-sulfonic acid affords B-2',3'-cyclic phosphate 5'-phosphosulfate

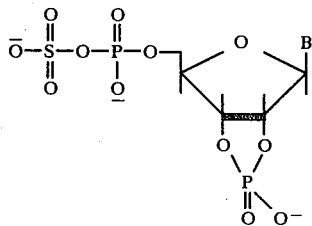 (III)

which, on treatment with ribonuclease T₂-RNase, provides the desired compound, 3'-phospho-B-5'-phosphosulfate (IV) like (PAPS).

The iso or II isomer may be prepared by treating III with spleen phosphodiesterase (PDase II) which converts III to the 2'-phospho B 5'-phosphosulfate

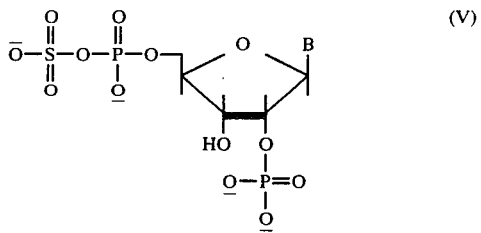 (V)

The biological activity of IV (like PAPS) may be measured by sulfate transfer to [6,7-$^3$H$_2$]estrone as mediated by bovine adrenal estrone sulfotransferase (3'-phosphoadenylylsulfate:estrone 3-sulfotransferase, EC 2.8.2.4) and is identical with that obtained with a sample of IV prepared by an established biochemical procedure. By the same contrast, V exhibits approximately one-third the activity of the natural isomer.

The Roman numerals correspond with those of the schematic above.

GENERALIZED PROCEDURE USING ADENINE AS B

The phosphorylation of adenosine (I) with pyrophosphoryl chloride followed by neutral buffered hydrolysis (cf. Simonscits and Tomasz, supra.) provides a convenient route to adenosine 2',3'-cyclic phosphate 5'-phosphate (II). Purification of II was achieved in the present invention by DEAE-Sephadex A-25 column chromatography using a linear gradient of triethylammonium bicarbonate (TEAB), pH 7.5 which afforded II in 62% yield.

The formation of the 5'-sulfatophosphate anhydride moiety (III) was effected with triethylamine-N-sulfonic acid. The requisite separation of III from the sulfating agent and tri-n-octylamine was readily accomplished on a column of Sephadex G-10 and elution with TEAB. Subsequent treatment of III with ribonuclease T₂ gave IV in yields of 68–72% (based on II) following column chromatography on DEAE-Sephadex A-25. The detection of 22% of adenosine 2'(3'),5'-diphosphate indicates that the conversion of II to III was in the order of 90%. A different enzyme PDase II hydrolyzed adenosine 2',3'-cyclic phosphate 5'-phosphosulfate (III) to V.

In agreement with the assigned structures it was found that acidic treatment of IV gave adenosine 3',5'-diphosphate with no chromatographic indication in either S₁ or S₂ of the presence of the 2',5'-isomer. The same conditions of hydrolysis applied to V gave adenosine 2',5'-diphosphate as the sole product.

Biological activity of IVa and Va was determined by sulfate transfer to [6,7-$^3$H$_2$]estrone in the presence of bovine adrenal estrogen sulfotransferase (E.C. 2.8.2.4). The activity of IV was virtually identical to that obtained with a sample of PAPS derived via the enzymatic procedure. By varying the concentration of IV between 15–100 μM and with [6,7-$^3$H$_2$]estrone maintained at 100 μM, saturation curves for IV from two sources were produced which were essentially superimposable. Iso-PAPS exhibited approximately one-third percent the activity of the natural isomer. Moreover, V showed fractional inhibition of estrone-sulfation (by IV) of 0.33 (unity = 100% sulfation).

The availability of adenosine 2',3'-cyclic phosphate 5'-phosphate (II) provides ready access to IV and V via III. The use of Sephadex G-10 column chromatography provides a facile and rapid separation of III from tri-n-octylamine and triethylamine-N-sulfonic acid. Enzymatic cleavage of the 2',3'-cyclic phosphate ester in III can be achieved to afford either IV or V using the requisite enzyme. Final purification of the products is conveniently effected on DEAE-Sephadex A-25 employing linear gradient elution of the column by TEAB.

PREPARATION OF THE ANALOGS

The preparation of the 3'-phosphoribonucleoside 5'-phosphosulfate utilized an approach identical with that used for the synthesis of 3'PAdo5'PS (IVa). Thus, treatment of a purine ribonucleoside (I) with pyrophosphoryl chloride followed by neutralization of the reaction mixture with triethylammonium bicarbonate buffer (pH 7.5), provided the requisite intermediate nucleoside 2':3'-phosphate 5'-phosphate (II) in good yields (52–83%) after purification via column chromatography on DEAE-Sephadex A-25 and removal of the buffer. Reaction of II with triethylamine N-sulfonic acid led to the corresponding 2':3'-phosphate 5'-phosphosulfate derivative (IIIb, c, d, e, and f). The latter, on treatment with ribonuclease-$T_2$, gave the analogs of 3'PAdo5'PS; i.e., IVb-f, in nearly quantitative yields following chromatography on DEAE-Sephadex A-25 with a linear gradient of 2 liters each of 0.05–1.5 M triethylammonium bicarbonate, pH 7.5.

The positional isomers of 2'P(7-deaza-Ado)5'PS (Ve) and 2'PFo5'PS (Vf) were obtained by the action of spleen phosphodiesterase on IIIe and IIIf respectively as for the conversion of IIIa to 2'PAdo5'PS (Va). Chromatography of Va on DEAE-Sephadex A-25 provided a product homogeneous in $S_1$, $S_2$, $E_1$, and $E_2$.

EXAMPLES

In the following Examples 1–5, in Table I, and with reference to Compounds I–V, "B" is adenine.

General Procedure

Bovine spleen phosphodiesterase II (E.C. 3.1.4.18) and ribonuclease $T_2$ were purchased from Sigma Chemical Company. Bovine adrenal estrogen sulfotransferase (E.C. 2.8.2.4.) was isolated and purified as described by Adams et al, *Biochim. Biophys. Acta,* 370:160–188 (1974). [$^{35}$S]PAPS and [6,7-$^3$H$_2$]-estrone were purchased from New England Nuclear Corp.

Thin-layer chromatography was performed in System $S_1$: saturated (NH$_4$)$_2$ SO$_4$/0.1 M ammonium acetate/2-propanol (79:19:2, v/v), and in System $S_2$: 1-propanol/conc. NH$_4$OH/H$_2$O (6:3:1, v/v) on precoated cellulose sheets (Polygram Cel 300 UV$_{254}$, Machery Nagel). Paper electrophoresis was performed in a Savant high voltage electrophoresis apparatus on Whatman No. 1 paper in Solvent $E_1$: 0.02 M Na$_2$HPO$_4$, pH 7 at 30 V cm$^{-1}$ for 1.5 h. Thin-layer electrophoresis was performed in a Brinkmann Desaga apparatus on pre-coated cellulose F plates (E. Merck) in Solvent $E_2$: 0.025 M sodium citrate, pH 5.4 at 15 V·cm$^{-1}$ for 2 h. $R_F$ values and electrophoretic mobilities are summarized in Table I.

TABLE I

Thin-Layer Chromatography and Electrophoresis of Compounds

| Compound | $R_F$ | | Mobility* | |
|---|---|---|---|---|
| | $S_1$ | $S_2$ | $E_1$** | $E_2$*** |
| Adenosine 5'-phosphate | — | — | 0.58 | 0.19 |
| IIα | 0.33 | 0.32 | 0.82 | 0.72 |
| IIIα | 0.33 | 0.48 | 0.99 | — |
| Adenosine 3',5'-diphosphate | 0.50 | 0.15 | 0.85 | 0.59 |
| IVα | 0.53 | 0.27 | 1.00 | 1.00 |
| Vα | 0.56 | 0.24 | 1.00 | 1.08 |
| Adenosine 2',5'-diphosphate | 0.59 | 0.15 | 0.85 | — |

*Relative to mobility of Compound IVα.
**Paper electrophoresis.
***Thin-layer electrophoresis.

Example 1

Preparation of Adenosine 2',3'-cyclic phosphate 5'-phosphate

This compound was prepared from adenosine (Compound Ia, 0.67 g, 2.5 mmol) using about 25 mmol of pyrophosphoryl chloride in tenfold relationship to adenosine at 0°–3° C. with stirring and without moisture by a modification of the method of Simoncsits and Tomasz, supra. After hydrolysis of the reaction mixture with 1.0 M triethylammonium bicarbonate at a pH 7.5 below 10° C., the buffer was removed by concentration to a small volume, followed by several evaporations with ethanol under reduced pressure at 30° C. The white residue was dissolved in 37.5 ml of 0.05 M triethylammonium bicarbonate and stored at −15° C. A 6 ml portion of the crude product (5525 A$_{259}$ units, one A$_{259}$ unit is that amount of material in 1 ml of solution that has an absorbance of 1.0 when it is measured with a 1.0 cm optical path at 259 nm) was chromatographed at 4° C. on a 2.5·35 cm column of DEAE-Sephadex A-25 with a linear gradient of 2 l each of 0.05–1.0 M triethylammonium bicarbonate, pH 7.5. Fractions (approx. 20 ml each) 78–97 contained 3800 A$_{259}$ units (62% yield, based on adenosine and $$\epsilon \frac{H_2O}{max} = 15\,400$$

for AMP) of Compound II. The buffer was removed in the usual manner and the product was frozen for storage in 5 ml of H$_2$O.

Example 2

Preparation of adenosine 2',3'-cyclic phosphate 5'-phosphosulfate (Compound IIIa)

To a solution of 2890 A$_{259}$ units of Compound IIa in 9.1 ml of ethanol was added 0.34 ml of tri-n-octylamine. The ethanol was removed under reduced pressure and the residue was rendered anhydrous by repeated evaporation from dimethylformamide at the oil pump. To the residue was added 3 ml of dimethylformamide, 3 ml of dioxane and 0.6 ml of pyridine and the mixture was shaken for 5 min. Then, 110 mg of triethylamine-N-sulfonic acid (high oral toxicity) was added and the reaction mixture was sealed and shaken overnight at room temperature. A thin-layer chromatogram in $S_2$ indicated that the major product was Compound IIIa. The solvents were removed at the oil pump and the residue was suspended in 6 ml of ice-cold H$_2$O containing 0.2 ml of 1.5 M NH$_4$OH. The mixture was adjusted to pH 7 and applied to a Sephadex G-10 column (2.6 . 40 cm), which had been pre-equilibrated at room temperature with 0.1 M triethylammonium bicarbonate in 20% ethanol. Elution was continued until 60 ml had been collected. Six 20 ml fractions then were collected and fractions 1–4 were pooled to give 2880 $A_{259}$ units. Buffer was removed in the usual manner. To the residue was added 5 ml of ice-cold $H_2O$ and the pH was adjusted to 5.9 with 1.5 M $NH_4OH$. Crude Compound III was used in the enzymatic transformations without further purification.

Example 3

Preparation of 3′-phosphoadenosine 5′-phosphosulfate (Compound IVa)

To the solution of Compound IIIa was added 0.2 ml (100 units) of an aqueous solution of ribonuclease $T_2$. After 20 h at room temperature a thin-layer chromatogram in System $S_2$ showed complete conversion of Compound IIIa to Compound IVa (cf Table I, supra). Chromatography on DEAE-Sephadex A-25 in the manner described for Compound IIa (Exammple 1) gave three major peaks. Peak 1 (fractions 104–122) contained 623 $A_{259}$ units (22%) of adenosine 3′,5′-diphosphate $$(\lambda_{max}^{H_2O} = 259 \text{ nm}).$$

Peak 2 (fractions 140–159) contained 1932 $A_{259}$ units (68%) of Compound IVa. Peak 3 (fractions 166–180) contained 196 $A_{259}$ units (7%) of an unidentified compound, which exhibited an anomalous ultraviolet spectrom $$(\lambda_{max}^{H_2O} = 262 \text{ nm}).$$

Fractions containing Compound IVa were pooled and the buffer was removed in the usual manner. The product was redissolved in approx. 3 ml of $H_2O$ and the solution was adjusted to pH 7 with dilute $NH_4OH$. Treatment of a small aliquot of the latter with an equal volume of 0.2 M HCl at 37° C. for 1.75 h gave adenosine 3′,5′-diphosphate as the sole detectable product in Systems $S_1$ and $S_2$. Compound IVa was homogeneous in $S_1$, $S_2$, $E_1$ and $E_2$. It exhibited a typical adenine nucleotide spectrum $$(\lambda_{max}^{H_2O} = 259 \text{ nm}, \lambda_{min}^{H_2O} = 227),$$

and it could be frozen for storage or kept indefinitely in 50% ethanol at −20° C. Compound IVa gave yields of 68–72% based on Compound IIa. Consonant with the assigned structures, it was found that acidic treatment of Compound IVa gave adenosine 3′,5′-diphosphate with no indication of the presence of the 2′,5′-isomer.

Example 4

Preparation of 2′-phosphoadenosine 5′-phosphosulfate (Compound Va)

To a solution of 790 $A_{259}$ units of crude Compound IIIa in 2 ml of $H_2O$, adjusted to pH 6 with 1.5 M $NH_4OH$, was added 0.4 ml (9 units) of a solution of spleen phosphodiesterase II in 0.05 M potassium acetate, pH 6. After 18 h at room temperature, chromatography in $S_1$ and $S_2$ showed approx. 40% formation of Compound Va. An additional 4.5 units of enzyme were added and the mixture was kept at room temperature for 18 h to complete the reaction. Compound Va was isolated in 89% yield following chromatography on DEAE-Sephadex A-25 in the usual manner. It was homogeneous in $S_1$, $S_2$, $E_1$ and $E_2$ and exhibited a typical adenine nucleotide spectrum ($\lambda_{max}$=259 nm, $\lambda_{min}$=227 nm). It moved slightly faster than Compound IVa in $S_1$ and $E_2$ but had nearly the same mobility as Compound IVa in Systems $S_2$ and $E_1$. After adjustment of pH to 7, Compound Va was frozen for storage at −15°. Hydrolysis of Compound Va under acid conditions gave adenosine 2′,5′-diphosphate as the sole product and the biological activity as compared with the natural isomer IVa was about 33%.

Example 5

Comparative sulfation of estrone by Compounds IVa and Va

Sulfation of estrone with synthetic Compound IVa (PAPS) was determined using the procedure described in the article by Rozhin et al, ante. Sulfation by Compound Va was as follows. The ability of Compound Va to donate its sulfate to estrone was determined with [6,7-$^3H_2$]estrone (1.3·10$^6$ dpm/4 nmol) by modification of the above-mentioned Rozhin et al method in which Compound Va (0.11 mM) is not substituted for Compound IVa.

After termination of the incubation, excess free [$^3$H]estrone was extracted three times with 0.3 ml of ethyl ether and the aqueous sample adjusted to 0.5 ml with redistilled methanol. An aliquot (25 μl) was applied, together with 15 μg of methanolic estrone sulfate marker, to type SG chromatography media (Gelman Instrument Co., Ann Arbor, Michigan) and developed with chloroform/acetone/acetic acid (110:35:6). Estrone sulfate was visualized by spraying with methylene blue and the spot punched out with a cork borer and counted in 10 ml of Bray's dioxane scintillation solution. Methylene blue did not affect counting efficiency. The amount of steroid sulfate ester produced was calculated utilizing the specific activity of [$^3$H]estrone.

The effect of Compound Va as an inhibitor of estrogen sulfotransferase was determined by adding the inhibitor (0.1 mM) to an incubation mixture containing 22 μM Compound IVa and [6,7-$^3H_2$]estrone (1.3·10$^6$ dpm/22 nmol). Results are expressed as fractional inhibition.

The biological test data is in keeping with the fact that it is well established that PAPS is the sulfate donor in the formation of sulfate esters of a wide range of biological compounds found in nature for which a corresponding spectrum of sulfotransferases of differing specificities are needed for sulfation of such diversified types of substrates as phenols, steroids, N-arylhydroxylamines and glycosides. The source of active sulfate in these transfer reactions is in all cases 3′-phosphoadenosine 5′-phosphosulfate (IVa).

Until now the pursuit of specificity studies of the sulfotransferases has been handicapped by the lack of a suitable synthesis to provide an adequate supply of pure IVa. It is noted that enzymatic preparations of active sulfate from adenosine triphosphate (ATP) are tedious, time-consuming and convenient for only very small quantities. The present process describes an expeditious approach to pure IVa (PAPS) and additionally may be utilized for the synthesis of analogs of IVa, such as those preceeding from guanosine or cytidine. Some additional analogs of PAPS in which the present process may be applied are 3'-phosphoinosine 5'-phosphosulfate, 3'-phosphonebularine 5'-phosphosulfate.

The synthetic approach to analogs of 3'PAdo5'PS (IVa) represents a successful extension of the methodology for a practical synthesis of active sulfate; i.e., IVa, where the starting material was adenosine. Thus, each ribonucleoside 2',3'-cyclic phosphate 5'-phosphate (II), derived from the action of pyrophosphoryl chloride on the precursory nucleoside (I), was converted to the corresponding 5'-phosphosulfate derivative (III) by the action of triethylamine sulfonic acid. Regiospecific cleavage of the cyclic phosphate moiety in III to the desired ribonucleoside 3'-phosphate 5'-phosphosulfate (IV) was achieved with ribonuclease-$T_2$.

If the cyclic phosphate intermediate is treated with bovine spleen phosphodiesterase (PDase II), opening of the cyclic phosphate residue leads to the positional isomeric ribonucleoside 2'-phosphate 5'-phosphosulfate. Accordingly, 2'P(7-deaza-Ado)5'PS (Ve) was obtained from IIIe in a manner identical to that described for the conversion of IIIa to the isomer of active sulfate (Va).

The enzymic transfer of sulfate from each of the analogs (IV and V) to estrone was determined at saturation levels of the steroid. The sulfating potential of the nucleotide is expressed as a relative sulfurylation rate (RSR, cf. Table III) at concentrations of 200 μM. The latter represents a level of $10 \times K_m$ that of IVa to be the optimum concentration for testing the specificity of the enzyme at a single concentration. Estrone sulfate, unlike 3'PAdo5'P, has little or no effect on the estrogen sulfotransferase reaction.

The relative sulfurylation rates of estrone by analogs of the cosubstrate (IVa) show a parallel with the Ki of corresponding structural analogs of the coproduct, 3'PAdo5'P for estrogen sulfotransferase-mediated esterification. Replacement, for example, of the 6-amino group of adenine by hydrogen as in 3'PPuo5'P and in particular by oxygen as in 3'PIno5'P results in a substantial loss of enzyme affinity. The low RSR values of 3'PPuo5'PS (IVc) and 3'PIno5'PS (IVd) are presumably a reflection of a comparable level of enzyme affinity. By contrast, certain modifications in the imidazole ring of the coproduct as 3'P(7-deaza-Ado)5'P and the 7-carbon isosteric analog, 3'PTuo5'P, produce an enhanced affinity. The same modification in IVa afforded sulfurylating agents; i.e., 3'P8Br-Ado5'PS (IVb) and 3'PTu5'PS (IVe) which compare favorably with active sulfate itself (cf. Table III). The 14–15% reduction in the RSR of IVb and IVe, relative to IVa, may be a result of increased inhibition by the corresponding coproducts. Thus, IVb and IVe at concentrations of 200 μM produce levels of coproducts calculated to reach 4 μM. Significant inhibition of estrogen sulfotransferase can be effected at the anticipated concentration of these coproducts. Accordingly, the RSR values of IVb and IVe are in all probability >1.

Other structural variations in the imidazole ring as, for example, a change to the C-nucleotide, lead to a coproduct, 3'PFo5'P, of intermediate affinity for the enzyme. The related cosubstrate 3'PFo5'PS (IVf) demonstrated a corresponding modest capacity to sulfurylate estrone.

The positional isomer of active sulfate, 2'PAdo5'PS (Va) shows approximately one-third the activity of the natural donor, although the coproduct 2'PAdo5'P is devoid of activity (Ki=∞). Of the several ribonucleoside 2',5'-diphosphates examined to date, only 2'P(7-deaza-Ado)5'P has an effect on the estrogen sulfotransferase reaction. The Ki of the latter compares favorably with that of 3'PAdo5'P (Cf. Table III). The RSR of 2'PTu5'PS (Ve), on the other hand, is relatively low—approximately the same as that of Va.

If cosubstrates IV and related coproducts, as suggested above, bind to the same site, the same does not appear to obtain with 2'-phosphate positional isomers.

TABLE II

Physical Constants of Some Analogs of 3'-Phospho- and 2'-Phosphoadenosine 5'-phosphosulfate.

| Compound | pH 7 $\lambda_{max}$ (nm) | Phosphate$^a$ Nucleoside | $R_f$ $S_1$ | $S_2$ | Electrophoretic Mobility $E_1^b$ | $E_2^c$ |
|---|---|---|---|---|---|---|
| 3'P8-BrAdo5'PS | 264 | 1.92±0.04 | 0.36 | 0.26 | 1.79 | 0.86 |
| 3'P(7-deaza-Ado)5'PS | 270 | 1.96±0.06 | 0.60 | 0.21 | 1.75 | 0.83 |
| 2'P(7-deaza-Ado)5'PS | 270 | 1.98±0.02 | 0.66 | 0.16 | 1.94 | 0.94 |
| 3'PFo5'PS | 294 | 1.90±0.01 | 0.56 | 0.15 | 2.13 | 0.80 |
| 2'PFo5'PS | 294 | 2.03±0.03 | 0.62 | 0.14 | 2.17 | 0.87 |
| 3'PIno5'PS | 248 | 2.01±0.04 | 0.75 | 0.23 | 1.92 | 1.07 |
| 3'PPuo5'PS | 262 | 1.90±0.01 | 0.61 | 0.34 | 1.84 | 1.06 |

$^a$Phosphate was determined according to Keleti et al, Handbook of Micromethods for Biological Sciences, pp. 83–84, Van Nostrand Reinhold, New York.
$^b$Relative to 5'AMP = 1.00.
$^c$Relative to 3'PAdo5'PS = 1.00.

TABLE III

Kinetic Parameters of Some Analogs of 3'-Phospho- and 2'-Phoshoadenosine 5'-Phosphosulfate and Coproducts

| Sulfurylated Nucleotides | Relative Sulfurylation Rate$^a$ | Desulfurylated Nucleotides | $Ki^b$ (μM) |
|---|---|---|---|
| 3'PAdo5'PS | 1.00 | 3'PAdo5'P | 7 |
| 3'P8-BrAdo5'PS | 0.86 | 3'P8-BrAdo5'P | 1.7 |
| 3'P(7-deaza-Ado)5'PS | 0.85 | 3'P(7-deaza-Ado)5'P | 0.6 |
| 3'PFo5'PS | 0.31 | 3'PFo5'P | 43 |
| 2'PAdo5'PS | 0.29$^c$ | 2'PAdo5'P | ∞ |
| 2'P(7-deaza-Ado)5'PS | 0.18 | 2'P(7-deaza-Ado)5'P | 5.3 |
| 3'PPuo5'PS | 0.11 | 3'PPuo5'P | 68 |
| 2'Pfo5'PS | 0.06 | 2'Pfo5'P | d |
| 3'PIno5'PS | 0 | 3'PIno5'P | 800 |

$^a$The relative Sulfurylation Rate (RSR) is a measure of utilization of cosubstrate analogs as compared to 3'PAdo5'PS (velocity of utilization of 3'PAdo5'PS at 200 μM concentration is taken as 1.00).
$^b$Data taken from Tables II and III of Horwitz et al, Biochim. Biophys. Acta, 480:376–381 (1977).
$^c$This value was obtained at 100 μM concentration but due to weak binding of the coproduct, 2'PAdo5'P, and because 100 μM is saturation concentration, the RSR at 200 μM concentration is expected to be very close to 0.29.
$^d$Ki not determined.

We claim:
1. A process for the preparation of

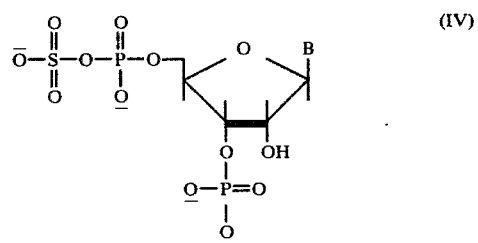

3'-phospho B 5'-phosphosulfate
where B is 8-bromoadenine, purine, hypoxanthine, 4-aminopyrrolo[2,3-d]pyrimidine (tubercidin), 7-aminopyrazolopyrimidine (formycin)
by the reaction of

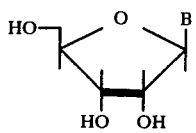

and pyrophosphoryl chloride to produce a substantially pure

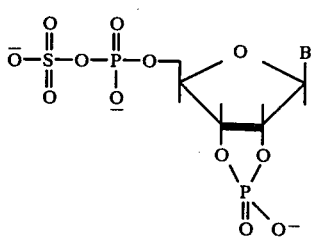

B-2',3'-cyclic phosphate 5'-phosphate and subsequently reacting II with triethylamine-N-sulfonic acid to produce B 2',3'-cyclic phosphate 5'-phosphosulfate which is further treated with ribonuclease-T$_2$ to provide 3'-phospho B 5'-phosphosulfate.

2. A process in which Compound III (B 2',3'-cyclic phosphate 5'-phosphosulfate) is treated with the enzyme spleen PDase II to produce

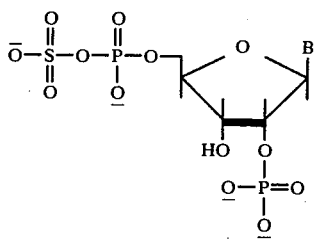

2'-phospho B 5'-phosphosulfate

3. The process according to claim 1 wherein the process is commenced with substantially pure pyrophosphoryl chloride II which is subsequently reacted with triethylamine-N-sulfonic acid and the product is subsequently treated with ribonuclease-T$_2$ to produce 3'-phospho B 5'-phosphosulfate.

4. A process of reacting Compound I with Compound II which is subsequently reacted with triethylamine-N-sulfonic acid and subsequently treated with spleen PDase to produce 2'-phospho B 5'-phosphosulfate.

5. The preparation of 2'-phospho B 5'-phosphosulfate (V) by a process reacting

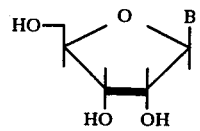

with pyrophosphoryl chloride to produce a pure B 2',3'-cyclic phosphate 5'-phosphate (II) and subsequently reacting said cyclic phosphate (II) with triethylamine-N-sulfonic acid to produce B 2',3'-cyclic phosphate 5'-phosphosulfate (III) and treating III with the enzyme spleen PDase to produce 2'-phospho B 5'-phosphosulfate (V) where B is selected from one member of the group consisting of 8-bromoadenine, purine, hypoxanthine, 4-aminopyrrolo[2,3-d]pyrimidine (tubercidin), and 7-aminopyrazolopyrimidine (formycin).

* * * * *